(12) United States Patent
Stefas (10) Patent No.: US 8,383,353 B2
(45) Date of Patent: Feb. 26, 2013

(54) METHOD FOR IN VITRO DETECTION AND/OR QUANTIFICATION AND/OR IDENTIFICATION OF INFECTIOUS COMPOUNDS IN A BIOLOGICAL MATERIAL

(75) Inventor: Ilias Stefas, La Grand Motte (FR)

(73) Assignee: Apoh Technologies SA, La Grande Mott (FR)

( * ) Notice: Subject to any disclaimer, the term of this patent is extended or adjusted under 35 U.S.C. 154(b) by 230 days.

(21) Appl. No.: 12/865,823

(22) PCT Filed: Jan. 30, 2009

(86) PCT No.: PCT/FR2009/000105
§ 371 (c)(1),
(2), (4) Date: Dec. 21, 2010

(87) PCT Pub. No.: WO2009/112702
PCT Pub. Date: Sep. 17, 2009

(65) Prior Publication Data
US 2011/0143353 A1    Jun. 16, 2011

(30) Foreign Application Priority Data

Feb. 1, 2008 (FR) ...................................... 08 00552

(51) Int. Cl.
*G01N 33/53* (2006.01)
*G01N 33/567* (2006.01)
*G01N 33/569* (2006.01)

(52) U.S. Cl. ............................ 435/7.1; 435/7.2; 435/7.32
(58) Field of Classification Search ........................ None
See application file for complete search history.

(56) References Cited

U.S. PATENT DOCUMENTS

| | | | |
|---|---|---|---|
| 5,344,758 A * | 9/1994 | Krilis et al. | .................... 435/7.1 |
| 5,650,269 A | 7/1997 | Rucheton et al. | |
| 6,465,191 B1 | 10/2002 | Stefas et al. | |

FOREIGN PATENT DOCUMENTS

| | | |
|---|---|---|
| EP | 0775315 A1 | 5/1997 |
| FR | 2723203 A1 | 2/1996 |
| FR | 2723204 A1 | 2/1996 |
| WO | WO9418569 A1 | 8/1994 |

* cited by examiner

*Primary Examiner* — Albert Navarro
(74) *Attorney, Agent, or Firm* — Browdy and Neimark, PLLC

(57) ABSTRACT

Method for in vitro detection and/or quantification and/or identification of bacteria present in a fluid medium M constituting a biological material, in which method a suspension of microbeads of solid polymer material capable of binding proteins is prepared; the microbeads are loaded with β2GPI proteins; said loaded microbeads are brought into contact with the fluid medium M, in the presence of ions of an oxidizing metal, so as to bind the bacteria to the β2GPI proteins; the microbeads thus prepared are separated from their suspension medium, so as to obtain a residue; and the bacteria of the residue are detected and/or quantified and/or identified.

12 Claims, 3 Drawing Sheets

Legends:
A : sample 7
T+ : positive control

FIGURE 6

METHOD FOR IN VITRO DETECTION AND/OR QUANTIFICATION AND/OR IDENTIFICATION OF INFECTIOUS COMPOUNDS IN A BIOLOGICAL MATERIAL

FIELD OF THE INVENTION

The present invention relates to a method for in vitro detection and/or quantification and/or identification of bacteria in a biological material.

BACKGROUND OF THE INVENTION

In the present description, by "biological material" is meant a biological tissue, a preparation or an extract originating from biological tissue, liquid or solid, or a medium, natural or not, capable of containing bacteria, for example flowing water or water for rinsing fruits and vegetables. Such a material can also be a mixture of at least two materials as defined above; it can therefore be, in particular, either prepared from tissues, organs, stools or body fluids from a patient suffering from a disease, or obtained from "in vitro" cultures; such biological material can be also a serum, plasma, urine, cerebrospinal fluid, synovial fluid, peritoneal fluid, pleural fluid, seminal fluid or acetic fluid.

A plasma glycoprotein called β2-glycoprotein I, or also abbreviated to "β2GPI", has already been described; the sequence of this human glycoprotein has in particular been referred to in the articles by J. LOZIER et al., Proc. Natl. Acad. Sci. ISA, Vol. 81, p. 3640-3644 (July 1984), and by T. KRISTENSEN et al., FEBS Letters, Vol. 289, p. 183-186 (1991). It has been noted that this β2GPI protein exhibits polymorphism: the name β2GPI is considered hereafter as generic for all forms.

In the international application WO 94/18569, it was pointed out that certain, in particular proteinaceous, infectious compounds bound to the form of β2GPI which had been described in French patent 2 701 263. In the document WO 94/18569, a method for detection and/or assay of viral compounds is proposed, in which the infectious viral compounds are bound to the form of β2GPI used; therefore this form of β2GPI is added to infectious viral compounds contained in a biological material, so as to separate the viral compounds thus captured in order to then detect them and/or assay them. In European patent EP 775 315, the formation of a complex between an infectious, in particular proteinaceous, compound and any form of β2GPI is described; the infectious compound could, in particular, be a bacterium. It is clear from these documents that the β2GPI is capable of binding to a flat solid support, such as the bottom of wells in a microtitration plate, and that the β2GPI thus adhering to this flat solid support, is capable of binding bacteria present in clinical, biological or environmental samples at very low concentrations. It is known, moreover, that such samples can contain substances inhibiting, at least partially, the detection of pathogens, substances which, as a result, can reduce the sensitivity of the detection. It is therefore important to be able to capture and concentrate these pathogens in order to eliminate the substances which inhibit their detection.

The studies of the Applicant company have shown that the binding of the β2GPI to the bottom of the wells in the titration plates, took place thanks to a particular conformation of the β2GPI, a conformation which subsequently allowed the formation of a complex of the β2GPI with an infectious compound. The literature had moreover reported that the conformation of the β2GPI varied at its binding to a solid surface (Matsuura et al., J. Exp. Med. 179, p. 457-462 (1994)). A method for the concentration of viruses had already been described (A. IWATA et al., Biol. Pharm. Bull. 26(8), p. 1065-1069 (2003)), using sulphonated magnetic microbeads to which the viruses would adhere, the concentration of the viruses being obtained due to the fact that the microbeads were magnetic and could be separated from the infectious medium by the action of a magnetic field. Unfortunately, the result of this technique was essentially a function of the adhesion of the viruses to the microbeads. This document explains in detail that certain non-enveloped viruses do not bind to beads made of polyethylene-imine and that it is necessary to use sulphonated microbeads in order to concentrate certain viruses. Moreover, for certain viruses, it was necessary to add bivalent cations. It follows from this finding that, depending on the nature of the virus, the polymer constituting the microbeads must be different, grafted or not grafted, and that bivalent ions are necessary or not necessary; the beads must therefore be prepared on an ad hoc basis depending on the virus to be concentrated. The same findings emerge from the document by E. UCHIDA et al., Journal of Virological Methods, 143, p. 95-103 (2007), which relates to the concentration of the human hepatitis A, B, and C viruses. In the presence of a sample containing an unidentified virus to be detected, it is not possible to determine what kind of microbeads is capable of giving rise to an adhesion of the virus of interest.

SUMMARY OF THE INVENTION

Consequently, given the existing drawbacks as regards binding viruses to microbeads, a person skilled in the art would not have been inclined to research binding bacteria to microbeads. The Applicant company has however gone against this adverse prejudgement by proposing, according to the present invention, to interpose a molecule of β2GPI between a microbead and a bacterium to be bonded above it. The state of the art has made it possible to determine the nature of the solid supports allowing good adhesion of β2GPI; the binding of the β2GPI to the microbead is then carried out without the polymer of the microbead having to be modified depending on the bacterium to be bonded subsequently. And, moreover, it was noted that the binding of the β2GPI to the microbead did not disturb the adhesion of the bacterium to the β2GPI; now, this last point was completely unexpected as it could not be foreseen that the conformation of the β2GPI bonded to a microbead, would allow the adhesion of a pathogenic agent to the glycoprotein. Incidentally and complementarily, a dissuasive element as regards arriving at the invention resulted from the fact that it was known that β2GPI had a tendency to self-polymerize (see: Thrombosis Research, 108, p. 175-180 (2003)), which risked leading to an agglutination of the microbeads carrying β2GPI, an agglutination which, of course, made the binding of pathogenic agents to the molecules of β2GPI unthinkable.

A subject of the present invention is consequently an in vitro method for detection and/or quantification and/or identification of bacteria present in a fluid medium M constituting a biological material, a method in which, in a known manner, a suspension of microbeads in a liquid suspension medium is prepared, said microbeads being delimited by an outer surface constituted by a solid polymer material capable of binding proteins, characterized by the fact that it comprises the following stages:

a) in an appropriate buffer, a loading of the microbeads in the suspension with β2GPI proteins is ensured by coupling with a sufficient quantity of β2GPI proteins, either passively in a suspension medium or using a known chemical binding protocol;

b) in a container, said microbeads loaded with β2GPI proteins are brought into contact with the fluid medium M, under appropriate conditions in order to ensure, without the presence of oxidizing metal ions, sufficient binding of the bacteria to the β2GPI proteins carried by the microbeads;

c) the microbeads thus prepared are separated from their suspension medium, said suspension medium is removed from the container in order to obtain a residue with a high concentration of bacteria;

d) and the bacteria in the residue are detected and/or quantified and/or identified.

It was quite surprising to note that, when the method defined above was implemented and the microbeads constituting the residue with a high concentration of bacteria were washed, the bacteria captured by the microbeads retained their ability to multiply. In an advantageous method of implementation, the method according to the invention is therefore characterized by the fact that the microbeads constituting the residue are washed, brought into contact with a culture medium capable of allowing their multiplication and, in a known manner, the bacteria are detected and/or quantified and/or identified starting from said culture medium. In order to allow the multiplication of the bacteria of the medium M bound to the microbeads, they are incubated under aerobic or anaerobic conditions on the culture medium for an appropriate period of time and at an appropriate temperature and the culture results obtained, the existence and/or the quantification and/or the identification of said bacteria are deduced. The fluid medium M can, in particular, be a haemoculture and, in this case, after obtaining the residue with a high concentration of bacteria and after washing it, the microbeads can be resuspended in a culture broth, for example a trypticase soy broth referred to as "TSB", and this broth can be applied to a blood culture medium, for example a "Columbia" sheep blood medium.

The bacteria can be identified by Gram staining and/or by subcultures, in selective or non-selective medium; bacteria can be quantified by optical density reading, by ATP-metry or by PCR.

The solid material constituting the outer surface of the microbeads is preferably chosen from the group formed by the plastics and the elastomers, said material carrying or not carrying reactive groups grafted to the outer surface of the microbeads in order to ensure a chemical bond to the β2GPI proteins; the microbeads can advantageously have a substantially spherical shape and an average diameter comprised between 1 and 100,000 nm. According to a first variant, the microbeads are separated from their suspension medium by centrifugation; but according to a second preferred variant, microbeads having a core formed by one (or more) particle(s) of magnetic material in order to allow their separation from the suspension medium using a magnetic field are chosen. Such magnetic microbeads are commercially available: for example, they are constituted by a magnetic core covered with a polymer matrix made of polystyrene. The magnetic field allowing the separation of the microbeads from their suspension medium can be created by a simple permanent magnet which is moved close to the container in order to carry out stage c) of the method according to the invention.

The choice of the material constituting the microbeads is limited only by its ability to couple the β2GPI: it is possible, for example, to use magnetic microbeads sold by MERCK under the trade name "Estapor® superparamagnetic microspheres". As indicated previously, the coupling of the β2GPI to the microbeads can be carried out either passively, or by using a chemical coupling protocol. In order to achieve passive coupling with the above-mentioned "Estapor"® microbeads, the microbeads are placed in suspension in a buffer containing β2GPI, at a pH comprised between 3.5 and 10.5 and, better, between 5.5 and 9.5. The buffer used is among the buffers commonly used in biology and can, in particular, be an acetate, phosphate, borate or Tris buffer. The microbead/β2GPI mixture is incubated at a temperature comprised between 4° C. and 40° C. for a period of time comprised between 10 nm and 24 h under stirring, preferably constant, gentle, horizontal stirring. The microbeads are subsequently separated magnetically or centrifuged and the supernatant is removed. The pellet containing the microbeads is placed in suspension in a preservation buffer, which is, preferably, the same as that used subsequently for the coupling, this buffer having a pH comprised between 6 and 9. Preferably, the loading of the microbeads with β2GPI proteins is carried out by placing them in a liquid suspension medium which contains, in aqueous solution, from $10^{-6}$ to 100 mg of β2GPI per gram of dry weight of microbeads, the concentration of β2GPI in the medium being then comprised between $10^{-5}$ and 10 μg/μl, and by stirring the suspension thus constituted for 15 to 60 nm at a temperature comprised between 30° C. and 45° C.

The sample containing the pathogen is brought into contact with the loaded microbeads, either directly, or after its dilution in a buffer, the pH of which is comprised between 5 and 9, preferably between 5.6 and 8. The complex which forms between the β2GPI and the pathogen is subsequently incubated for a period of time comprised between 5 nm and 24 h, preferably between 30 nm and 2 h at a temperature comprised between 4° C. and 40° C., preferably approximately 37° C. After incubation, the sample which has not reacted with the β2GPI bound to the microbeads, is removed by centrifugation or magnetizing of the microbeads. The microbeads thus isolated can be used for the detection and/or the quantification and/or the identification of the pathogen. The separation and/or the assay and/or the quantification of the pathogen bound to the support by the β2GPI can be carried out by any known means such as infectivity, a specific enzymatic reaction, a fluorescent or radiolabelled tracer, the detection of specific nucleic acid by hybridization with a labelled probe, a polymerase chain reaction (so-called "PCR"), an assay, a count, a visualization, an optical method, electron or non-electron microscopy.

In order to provide a better understanding of the subject of the invention, a description will now be given of several methods of implementation, as purely illustrative and non-limitative examples.

EXAMPLE 1

Binding of a Bacterium to Microbeads Loaded with β2GPI

The bacterium used is a strain of *Escherichia coli* (*E. coli*) supplied by the Centre de conservation de produits agricoles (CPA). A pre-culture is incubated at 37° C. for 16 h in LB (Luria Bertani) medium having the following composition:

| | |
|---|---|
| Bacto tryptone | 10 g |
| Yeast extract | 5 g |
| NaCl | 10 g |
| pH | 7.5 |
| Water | qsf 1,000 g |

This pre-culture is used immediately or stored at 4.5° C.

The microbeads intended for binding the bacteria which are used in this example are magnetic microbeads sold by MERCK under the name "Estapor® superparamagnetic microspheres" which have a diameter comprised between 0.300 and 0.500 µm.

These microbeads are placed in suspension in an acetate buffer with a pH of 6.0 containing the β2GPI. The concentration of β2GPI in this coupling buffer is 100 µg/ml; the microbeads are incubated in the buffer under constant gentle stirring at a temperature of 25° C. for 3 hours. The microbeads are then centrifuged at 1,500 rpm and the supernatant is removed; the centrifugation pellet is placed in suspension in the same buffer as that used for the coupling of the β2GPI, which forms the suspension of microbeads loaded with β2GPI to be tested.

The cultures of bacteria to be studied are placed in 1 ml haemolysis tubes with different quantities of microbeads depending on the tubes. The tubes are placed under horizontal stirring in order to mix the microbeads thoroughly and each tube is incubated at 37° C. or at ambient temperature (AT=22° C.); the incubation time is variable depending on the experiment carried out. In each tube, the microbeads are then separated from the liquid phase using a magnet place placed externally against the wall of the tube and the optical density (OD) of the supernatant at 600 nm is measured with an "Eppendorf" spectrophotometer.

Figure 1:
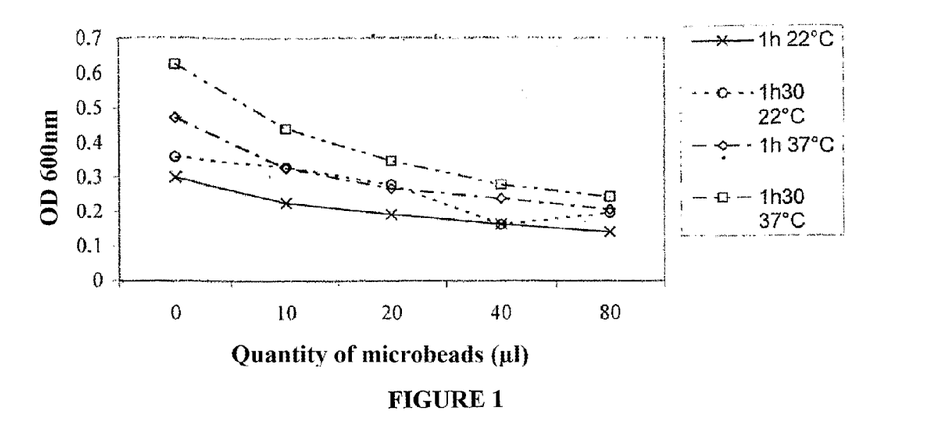
FIG. 1 is a graph showing quantity of microbeads versus optical density.
Figure 1A:
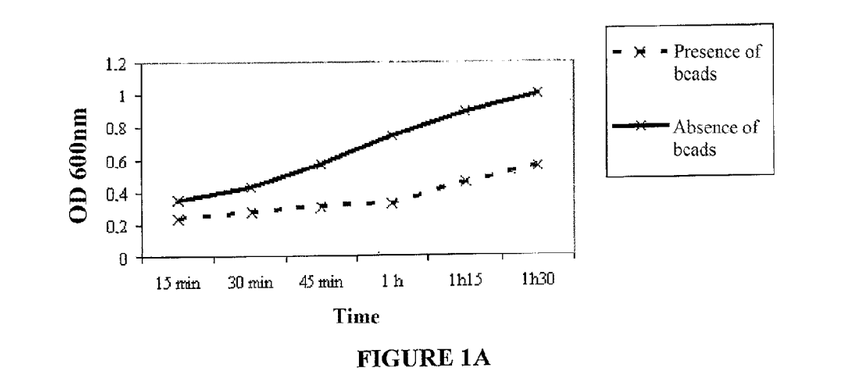
FIG. 1a is a graph showing optical density over time.

In the absence of microbeads, the OD at the start of the experiment is equal to 0.2 and it increases over time according to normal bacterial growth; in the presence of microbeads, the OD remains almost stable for approximately an hour then increases as in the absence of microbeads (see FIG. 1A). This suggests that the bacteria have bound to the microbeads, which has delayed the normal bacterial growth. FIG. 1 shows that, for the same quantity of microbeads and the same incubation time, the OD is greater when the incubation temperature is higher, which is normal for a bacterium of the digestive tract of mammals, the optimum growth of which is situated around 37° C. It will also be noted, in this same figure, that for the same incubation temperature, the greater the incubation time the greater the OD. Finally it will be noted in FIG. 1 that, for an incubation of given duration and temperature, the OD decreases when the quantity of microbeads increases.

The microbeads were also incubated with the buffered culture of *E. Coli* for 1 h 30 under stirring. As previously, the microbeads were separated magnetically and the supernatants were removed; the microbeads were washed with "fresh" LB culture medium and with a PBS solution corresponding to the following formulation:

| | |
|---|---|
| NaCl | 80 g |
| KCl | 74.562 g |
| $KH_2PO_2$ | 2.4 g |
| $Na_2HPO_4/2H_2O$ | 29 g |
| Water | qsf 1,000 g |

Figure 2:
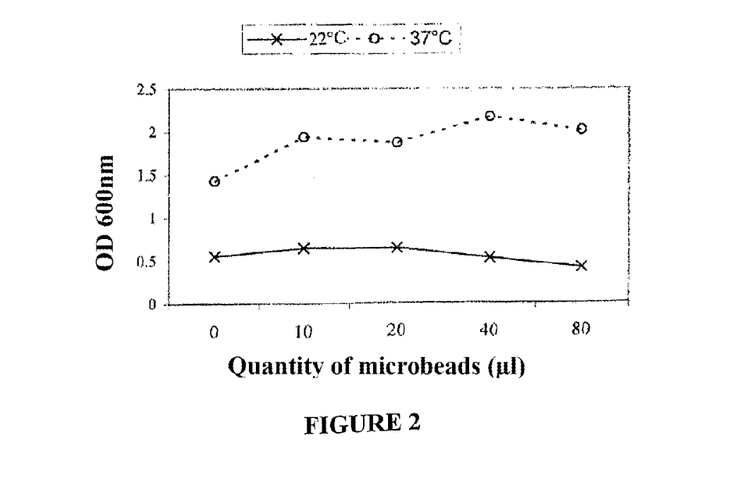
FIG. 2 is a graph showing measurement of optical density as a function of the quantity of microbeads initially introduced into the E. Coli culture.

The culture medium is left to incubate overnight at 37° C. or 20° C. and the OD is measured. The results are provided in FIG. 2 as a function of the quantity of microbeads initially introduced into the *E. Coli* culture. It is noted that the OD changes little as a function of the quantity of microbeads after incubation at 20° C., whereas it increases with the quantity of microbeads in the case of incubation at 37° C.

The physiological state of the bacteria captured by the microbeads has also been studied. An assay of the ATPs (adenosine tri-phosphates) and of the intracellular adenyl nucleotides (ANs) of the bacteria is carried out. It is known that ATP is an indicator specific to the living cell as, after cell death, it is very rapidly degraded to ADP (adenosine di-phosphate) and AMP (adenosine monophosphate) by ATPases. It is known, moreover (French Patent Application 04-11084 filed 19 Oct. 2004) that the sum ATP+ADP+AMP remains constant and equal to AN during cell growth. The quantities of ATP and of AN present on the microbeads after contact with *E. Coli* were measured by bioluminescence.

In order to carry out these measurements, haemolysis tubes were used, in which 10 µl of microbeads loaded with β2GPI were placed, which were incubated with 1 ml of the bacterial pre-culture for different incubation times at a temperature of 37° C. The beads are then separated by magnetizing (i.e. attraction by a permanent magnet outside the tube) in order to recover the supernatant then washed with fresh medium.

After a new magnetizing process, 200 μl of extractant and 1 ml of a buffer solution are added to each tube, these two reagents being supplied by "Control Life Technologies". This extractant is left to react for 10 nm in order to:

- cause the rupture of the envelopes of the bacteria in order to release the nucleotides;
- rapidly inhibit the enzymatic reactions, in particular ATPasic;
- have a minimal destructive effect on the ANs.

Each sample is divided into four 100 μl parts which are placed in four small rhesus tubes, two of which contain 5 μl of solution of lyophilized enzymes namely: phosphoenolpyruvate, adenylate kinase and pyruvate kinase; in the tubes of enzymes, the AMP and the ADP are converted to ATP. Therefore two (SE) tubes are obtained which have not undergone the enzymatic action and two (E) tubes which have undergone it. 5 μl of the luminous detector of ATP (luciferine/luciferase) is added to the four tubes and one (E) tube and one (SE) tube are passed through a luminometer (Control Life 300), where the light emission is measured for 5 s (result given in relative light units (RLU)). With the two remaining tubes, a second measurement is carried out after adding 5 μl of standard ATP (10 pmol/μl) to each tube: the result is used in order to correct the errors due to any inhibition of the light emission as knowing the second measurement makes it possible to convert the first to picomoles.

Figure 3:
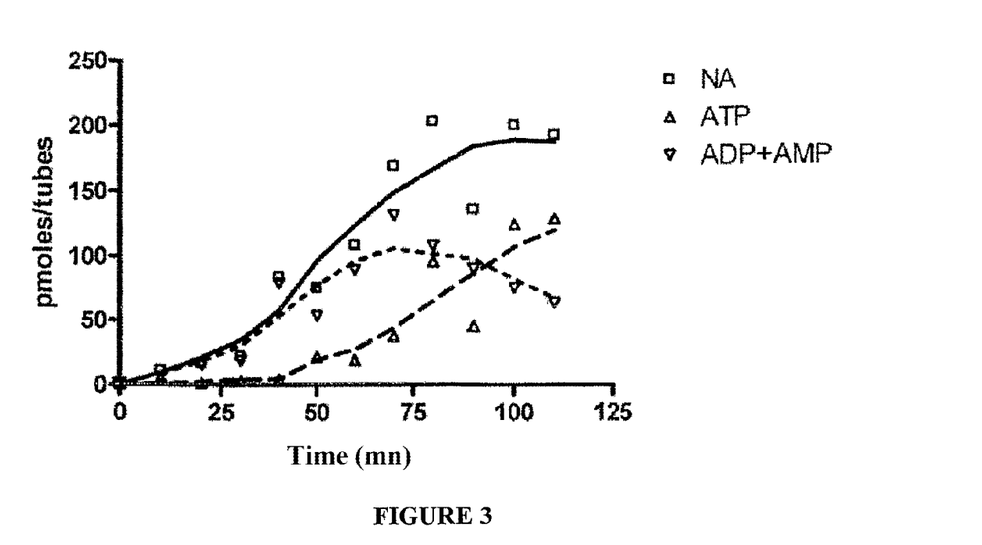
FIG. 3 and FIG. 4 show results of the measurements of ATP and AN in a tube were carried out as a function of the quantity of microbeads used in the tube.
Figure 4:
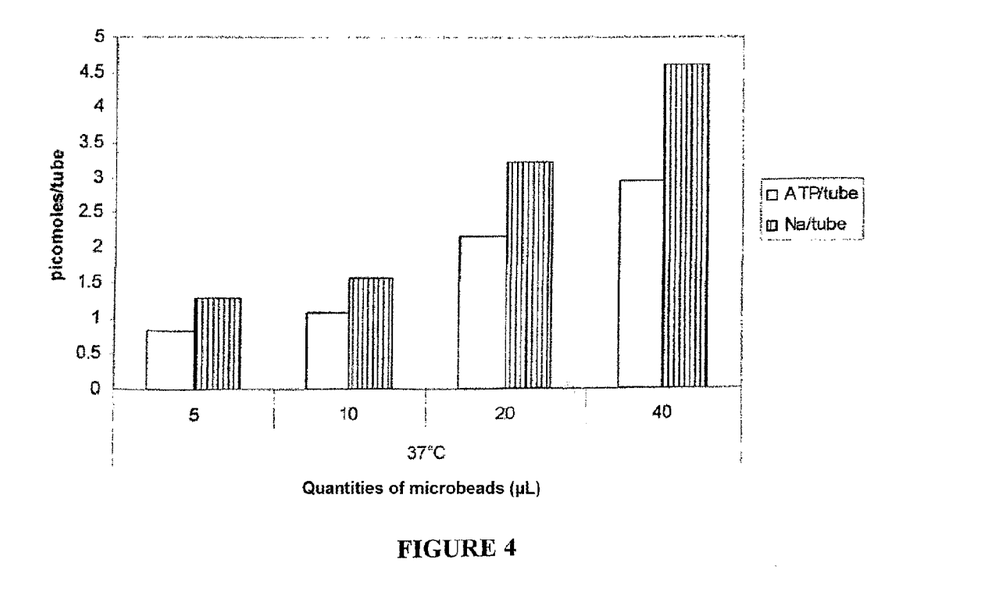

The results are given in FIGS. 3 and 4.

FIG. 3 shows an increase in the intracellular ANs present on the microbeads as a function of time and a saturation of the microbeads with ANs as from a time of approximately 80 nm of contact between the microbeads and the initial culture of bacteria. The quantity of ATP present on the microbeads increases with the microbeads/culture contact time; a saturation is noted corresponding to the fact that the capture of the bacteria by the microbeads depends on the surface of the microbeads used; moreover, given that the ATP content of a cell is representative of its activity, it can also be deduced from this that the microbeads capture the bacteria and bind the most active bacteria.

Moreover, the measurements of ATP and AN in a tube were carried out as a function of the quantity of microbeads used in the tube, the incubation for the capture of the bacteria being carried out for all the tubes at 37° C. for 1 h 30 under stirring: the results are given in FIG. 4. An increase in the ATP and intracellular ANs is noted when the quantity of microbeads increases. This confirms that the microbeads capture the bacteria present in the medium.

It is known that, in the case of bacteria (see D. CHAMPIAT, Biochimie luminescence et biotechnologie, Technoscope No. 51, Biofutur No. 110 and CHAMPIAT D. et LARPENT J P., Biochimie luminescence: Principes et applications, Edition Masson 1993), if the ATP/AN energy charge is comprised between 0.5 and 0.75, the bacteria are in growth phase. Table I below was compiled using the experimental values corresponding to FIG. 4 and shows that the ATP/AN ratio for a microbeads/bacteria contact carried out at 37° C., is comprised between 0.5 and 0.7.

TABLE I

| Temperature | 37° C. | | | |
|---|---|---|---|---|
| Quantity of microbeads | 5 μl | 10 μl | 20 μl | 40 μl |
| ATP/AN | 0.64 | 0.69 | 0.67 | 0.64 |

The microbeads therefore bind the bacteria in growth, i.e. in full metabolic activity. The capture of $E.\ Coli$ on the microbeads does not therefore inhibit the bacterial metabolism. As has already been indicated above with respect to FIG. 2, the bacteria, which have been bound to the microbeads, generate, on an appropriate medium and at an appropriate temperature, a culture, the OD of which increases as a function of the concentration of microbeads, which means that, despite their capture by the microbeads, the bacteria continue to multiply.

This set of results shows that bacteria are captured by the microbeads up to a saturation due to the quantity of microbeads loaded with β2GPI which is used. The microbeads do not inhibit the bacterial growth and do not lead to the death of the bacteria captured.

Analogous tests were also carried out with the bacteria *Pseudomonas aeruginosa, Streptococcus pneumoniae* and *Staphylococcus aureus* and produced the same type of results.

EXAMPLE 2

Interaction of β2GPI with the Bacteria Present in Human Blood

The microbeads used are the same as those the preparation of which was described in detail in Example 1.

Two series of haemocultures were used (haemocultures I comprising 5 samples and haemocultures II comprising 35 samples), originating from hospital samples. These haemocultures are carried out by placing a veinous blood sample (approximately 10 ml) in aerobic and anaerobic bottles of BacT/ALERT®3D type. These bottles are then incubated in an automatic device at 35° C. for at least 5 days. The bottles are equipped with a system of colorimetric detection using a sensor situated at the base of each bottle. The carbon dioxide produced by the bacteria in growth, causes the colour of the sensor to change; this change of colour is detected by the automatic device and indicates the presence of bacterial growth: these haemocultures are referred to as positive. In the BacT/ALERT®3D bottles there are particles of activated carbon which inhibit the antibiotics potentially present in the patients' blood, the detection of the microorganisms thus being improved. In order to confirm the presence of the bacteria in the haemocultures which have been revealed positive in the automatic device, the hospital carries out a culture on blood agar. The set of results originating from the hospitals thus makes it possible to identify

- positive haemocultures (positive in the automatic device and positive in culture),
- negative haemocultures (negative in the automatic device)
- and falsely positive haemocultures (positive in the automatic device and negative in culture).

In order to test the interaction of the microbeads loaded with β2GPI with the bacteria present in the blood, 1 ml of haemoculture is taken for each sample and placed in a 15 ml tube. Different quantities of microbeads loaded with β2GPI are added and each tube is incubated at 37° C. under horizontal stirring. The samples are then decanted into 2 ml silicone tubes. The tubes are placed in a magnetic field which holds the microbeads on the wall and the supernatant is removed. The microbeads are then washed twice with sterile PBS of the same composition as indicated previously in Example 1; the microbeads are then resuspended in 150 µl of TSB (trypticase soy broth) culture medium having the following formulation:

| | | |
|---|---|---|
| Casein peptone | 17.0 | g |
| Soy flour peptone | 3.0 | g |
| D(+)-glucose | 2.5 | g |
| Sodium chloride | 5.0 | g |
| Dipotassium phosphate | 2.5 | g |
| Water | qsf 1,000 | g |

This TSB culture medium was brought to the boil then autoclaved in order to render it sterile before use.

50 µl of the suspension of microbeads thus obtained is removed and deposited in a Petri dish on a "Columbia" sheep blood medium, referred to as "blood agar" (Laboratoires BioMérieux); this agar, bright red in colour, contains red blood cells: it constitutes a rich non-selective medium, which allows the growth of most of the bacteria of medical interest. The Petri dishes are incubated in an oven at 37° C. for 24 hours. This protocol makes it possible, with the microbeads, to detect bacteria present in the haemocultures. Three methods for detection of the bacteria captured by the microbeads, have been used: ATP-metry, culture on blood agar and PCR (Polymerase Chain Reaction) followed or not followed by sequencing.

A) Haemocultures I a) ATP-Metry

The method of ATP-metry used is identical to that used in Example 1. For each of samples 1, 2, 6, 7 and 8, 3 times 1 ml were taken and deposited in 15 ml tubes, producing 3 sub-samples. The 15 sub-samples were incubated at 37° C., with incubation times of 30, 60 or 90 minutes for the 3 sub-samples of the same sample.

Figure 5:
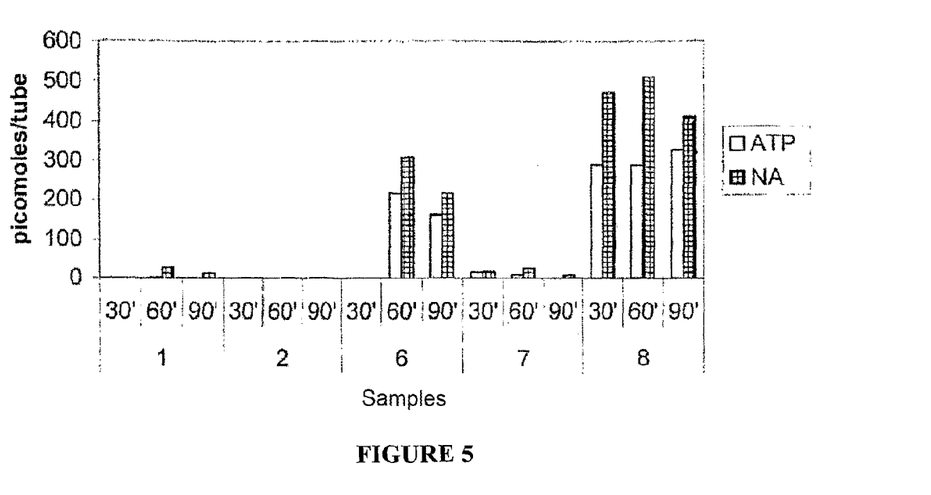
FIG. 5 is a graph showing the quantity of microbeads in the tested samples.

No bacteria were detected in samples 1, 2 and 7, independently of the quantity of microbeads or of the incubation time. On the other hand, bacteria were detected in samples 6 and 8 and the results are provided in FIG. 5. These results which relate to the 5 samples correspond to those obtained by the automatic device. Table II below gives the results corresponding to the energy load calculations relating to the results in FIG. 5: it is noted that the bacteria present in haemocultures 6 and 8 are in growth phase.

TABLE II

| Incubation time on | Sample 6 | | | Sample 8 | | |
|---|---|---|---|---|---|---|
| sub-sample (in mn) | 30 | 60 | 90 | 30 | 60 | 90 |
| ATP/AN | / | 0.70 | 0.74 | 0.61 | 0.56 | 0.79 |

This first part of Example 2A) establishes that the microbeads loaded with β2GPI capture the bacteria present in the haemocultures.

b) Culture

The bacteria bound with the different concentrations of microbeads in samples 1, 2, 6, 7 and 8 as indicated under a) above are cultured on blood agar. The results obtained on these samples after incubation for 24 h at 37° C., are presented in Table III below. For haemocultures 6 and 8, the culture confirms the results found separately at the hospital, which demonstrates that the microbeads do indeed capture the bacteria present in the tubes.

TABLE III

| Sample No. | Germs identified at the hospital | Culture condition | Germs identified according to the invention on blood agar | | | | Gram staining |
|---|---|---|---|---|---|---|---|
| | | | Without microbeads | Quantity of microbeads | | | |
| | | | | 25 µl | 50 µl | 75 µl | |
| 1 | negative | aerobic | / | / | / | / | / |
| | | CO$_2$ | / | / | / | / | |
| 2 | negative | aerobic | / | + | | / | (−) bacillus = |
| | | CO$_2$ | / | / | / | / | Pseudomonas |
| 6 | Pseudomonas | aerobic | + | ++ | +++ | ++++ | (−) bacillus = |
| | | CO$_2$ | + | ++ | +++ | ++++ | Pseudomonas |
| 7 | negative | aerobic | / | / | 100 colonies with haemolyses | 2/3 colonies with haemolyses | Cocobacilli (−) |
| | | CO$_2$ | / | / | ++++ with haemolyses | 4 colonies with haemolyses | |
| 8 | S. marescens | aerobic | + | ++ | +++ | ++++ | (−) bacillus = |
| | | CO$_2$ | + | ++ | +++ | ++++ | Pseudomonas |

In order to identify the bacterial colonies, Gram stainings and sub-cultures were carried out on different selective or non-selective media. For haemoculture No. 7, the identification at the hospital produced a negative result whereas colonies were obtained using microbeads. Gram staining was carried out: the result indicated that a Gram positive coccobacillus was involved; the coccobacillus being an intermediate form between a bacillus and cocci, this was seeded on the following media: MacConkey medium, Chapman medium, TS medium, Cetrimide medium. These media correspond to the following formulations:

TABLE IV

| Medium | Chapman | T.S. | MacConkey | Cetrimide |
|---|---|---|---|---|
| Peptone | 10 g | | 20 g | |
| Caseine trypsic peptone | | 15 g | | |
| Papainic soy peptone | | 5 g | | |
| Gelatin peptone | | | | 16 g |

TABLE IV-continued

| Medium | Chapman | T.S. | MacConkey | Cetrimide |
|---|---|---|---|---|
| Lactose | | | 10 g | |
| Bile salts no. 2 | | | 1.5 g | |
| Beef extract | 1.0 g | | | |
| Sodium chloride | 75 g | 5 g | 5 g | |
| Mannitol | 10 g | | | |
| Phenol red | 0.025 g | | | |
| Crystal violet | | | 0.001 g | |
| Neutral red | | | 0.05 g | |
| Tetradonium bromide (cetrimide) | | | | 0.2 g |
| Nalidixic acid | | | | 15 g |
| Potassium sulphate | | | | 10 g |
| Magnesium chloride | | | | 1.4 g |
| Agar-agar | 15 g | | 15 g | |
| Agar | | 15 g | | 10 g |

The results showed that this bacterial strain grew on all the media.

c) PCR and Sequencing Method

A PCR was then carried out followed by a sequencing of the 16S rDNA.

The bacterial DNA is extracted from the bacteria which have been captured by the microbeads; the bacteria are lysed by adding 100 µl of "Chelex 30%" to the microbeads. The mixture is incubated for 10 minutes at 95° C.; then centrifugation is carried out for 10 minutes at 10,000 rpm. The supernatant containing the DNA is stored at −20° C.

47 µl of the amplification solution (AquaPure Genomic DNA Isolation KIT) is added to 3 µl of the extracted DNA; the final concentrations are as follows:

5 µl: 200 mM dXTP
10 µl: BUFFER 5×
5 µl: 2 mM MgCl$_2$
1 µl of each primer: primer diluted to 200 mL:

27 f: GTGCTGCAGAGAGTTTGATCCTGGCTCAG (SEQ ID NO: 1)

1492 r: CACGGATCCTACGGGTACCTTGTTACGACTT (SEQ ID NO: 2)

1 µl Taq polymerase, 5 u/µL
WFI water qsf 50 µL

After homogenization, the reaction mixtures are placed in an "Eppendorf" thermocycler and subjected to the following programme:

$$\left.\begin{array}{l} 94°\text{ C.: 1 mn} \\ 60°\text{ C.: 1 mn} \\ 72°\text{ C.: 2 mn} \end{array}\right\} 35 \text{ cycles}$$
$$72°\text{ C.: 10 mn}$$

The DNAs are then maintained at 10° C. The migration takes place on a 2% agarose gel in PBE buffer 0.5× containing ethidium bromide. The gel is then observed under UV light.

Figure 6:
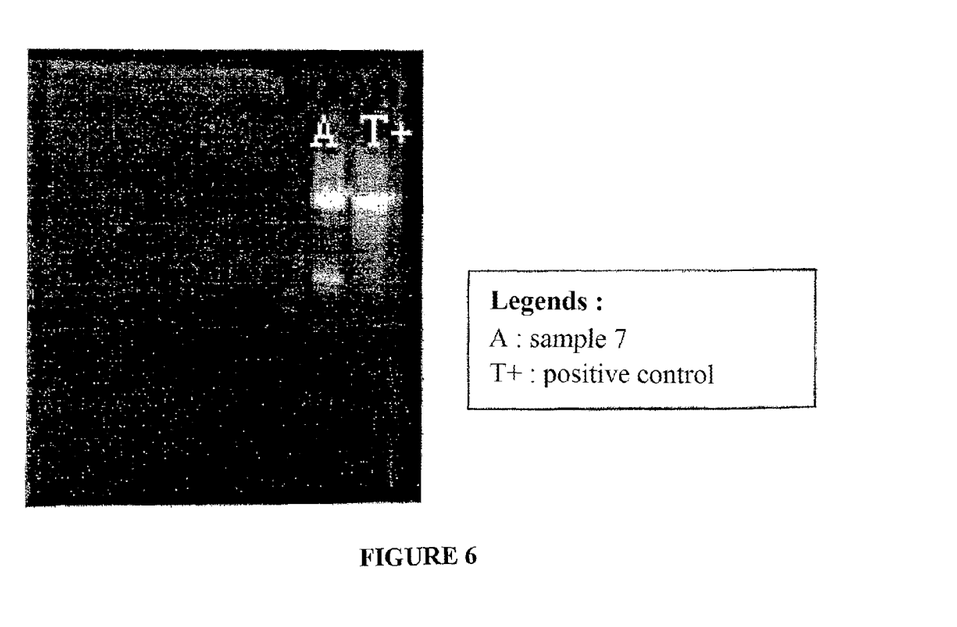
FIG. 6 show a PCR tests on the samples showing the presence of bacterium.

The results of the PCR clearly indicate the presence of a bacterium: a strong positive signal is noted (see FIG. 6). The identification of the bacterium can then be carried out by sequencing in a known manner.

It is therefore noted that the method according to the invention makes it possible, thanks to the use of microbeads loaded with β2GPI, to detect and identify bacteria in human blood whereas the standard methods implemented at the hospital do not allow this.

B) Haemocultures II

The technique defined at the start of Example 2 is implemented: 1 ml of a haemoculture is placed in a 15 ml tube, and a certain quantity of microbeads loaded with β2GPI (here 25 or 50 µl) is added and left to incubate in the medium. The microbeads are then separated magnetically, washed and re-suspended in a sterile buffer. This suspension is deposited on a blood agar in a Petri dish and incubated for 24 hours at 37° C. The set of haemocultures tested corresponds to Table V below:

TABLE V

For the positive haemocultures, the microbeads make it possible to confirm the results obtained by an automatic device and by culture at the hospital. The microbeads therefore do indeed capture the bacteria present in the haemocultures.

For certain samples, with 25 µl and 50 µl of microbeads, the results suggest the presence of a second type of bacteria not detected at the hospital. After identification, it was noted that this was a *staphylococcus* (Gram-positive cocci). In the case of the samples 5054 containing *S. HOMINIS* and 5060 containing *P. MIRABILIS* obtained from the same person, both bacteria were detected on blood agar in each of the two samples, contrary to the results given by the hospital.

For the negative haemocultures, the beads made it possible to confirm the results found at the hospital, except for haemoculture 2081 where the microbeads demonstrated bacteria of Gram-positive coccus type (Staphylococus). In the false positives, the microbeads also made it possible to detect bacteria of Gram-positive cocci type, in the case of two of the nine haemocultures tested. It is noted that among the haemocultures which had been found negative at the hospital, one haemoculture proved positive when the microbeads were cultured on blood agar, which shows that the invention makes it possible to improve the sensitivity of the detection.

Tables VA, VB, VC and VD below summarize the results found:

TABLE VA

| | | Culture under aerobic conditions: | | | |
|---|---|---|---|---|---|
| | Germs | Germs identified on blood agar, according to the invention | | | |
| Haemoc No. | identified at the hospital | Without microbeads | 25 μL of microbeads | 50 μL of microbeads | Gram |
| 1052 | *K. pneumoniae* | Opaque colony: +++ white colony: + | Opaque colony: +++ | opaque colony: +++ white colony: + | |
| 2058 | *S. epidermidis* | White colony: ++ Yellow colony: + PS: presence of haemolysis around the colonies. | White colony: ++ Yellow colony: + PS: presence of haemolysis around the colonies. | White colony: ++ Yellow colony: + PS: presence of haemolysis around the colonies. | Carried out in the mass: (+) Cocci = *S. epidermidis* and beads |
| 1481 | *E. fecaelis* | Colony 1: ++ | Colony 1: ++ | Colony 1: ++ Colony 2: + | Colony 1: (+) cocci = *E. fecaelis* Colony 2 (+) cocci |
| 7051 | *E. coli* | Colony 1: +++ | Colony 1: ++ | Colony 1: ++ | |

| | Haemoc No. | Isolation of Gram + bacteria | | | |
|---|---|---|---|---|---|
| | | On blood agar | On Chapman | On M.K | Gram |
| | 1052 | Opaque colony ++ white colony ++ | | | (−) *bacillus* = *K. pneumoiae* (−) *bacillus* = *K. pneumoiae* |
| | 2058 | White colony ++ Yellow colony / | | | Cocci (+) |
| | 1481 | Colony 2 ++ | Colony 2 + | | Colony 2 (+) Cocci = *Staphylococcus* |
| | 7051 | | | | |

TABLE VB

| | | Cultures under aerobic conditions: | | | |
|---|---|---|---|---|---|
| | Germs | Germs identified on blood agar, according to the invention | | | |
| Haemo No. | identified at the hospital | Without microbeads | 25 μL of microbeads | 50 μL of microbeads | Gram |
| 5054 | *S. hominis* | colony 1: +++ | colony 1: +++ colony 2: + | colony 1: +++ colony 2: + | Colony 1: (+) Cocci *S. hominis* Colony 2: (−) *Bacillus P. mirabilis* |
| 4351 | False + | / | 25 colonies: certain with haemolysis and others without haemolysis | / | (+) Cocci |
| 7059 | *E. coli* | Colony 1: ++ | Colony 1: + Colony 2: a single white colony | Colony 1 ++ | Colony 1: coccobacillus |

TABLE VB-continued

Cultures under aerobic conditions:

| | | | | | |
|---|---|---|---|---|---|
| 5060 | *P. mirabilis* | Colony 1: +++ | colony 1: +++ <br> colony 2: + | colony 1: +++ <br> colony 2: + | Colony 2: <br> (+) Cocci = <br> *S. hominis* <br> Colony 1: <br> (−) *Bacillus* = <br> *P. mirabilis* |

| Haemo | Isolation of Gram + bacteria | | | |
|---|---|---|---|---|
| No. | On blood agar | On Chapman | On M.K | Gram |
| 5054 | | Colony 1 / <br> Colony 2 ++ | Colony 1 + <br> Colony 2 / | |
| 4351 | With haemo. ++there is haemolysis) <br> Without haemo. ++there is haemolysis) | A colony was isolated | + | (+) Cocci |
| 7059 | Colon2 + | Colony 2 | ++ | Colony 1: ++ | Colony 2: <br> (+) Cocci <br> *Staphylococcus* <br> Colony 1: <br> (−) *Bacillus* <br> *E. coli* |
| 5060 | | Colony 1 + <br> Colony 2 / | Colony 1 / <br> Colony 2 ++ | |

TABLE VC

Cultures under aerobic conditions:

| N° haemo. | Germs identified at the hospital | Germs identified on blood agar, according to the invention | | | Gram |
|---|---|---|---|---|---|
| | | Without microbeads | 25 μL of microbeads | 50 μL of microbeads | |
| 5055 | *S.hominis* | Colony 1: ++ | Colony 1: ++ | Colony 1: ++ | |
| 7096 | *S.bovis* | / | / | / | |
| 3353 | *E.coli* | Colony 1: ++ | Colony 1: ++ | Colony 1: ++ | |
| 3013 | *L.monocytogenes* | Colony 1: ++ | Colony 1: ++ | Colony 1: ++ | |
| 3053 | *Corine bacterium*.sp | after 24 h: / <br> after 48 h: ++ | after 24 h: / <br> after 48 h: ++ | after 24 h: / <br> after 48 h: ++ | Irregular (+) bacillus which grows on the microbeads. Therefore gives the impression of a second colony |
| 2081 | Negative | / | 8 colonies | 15 colonies | (+) Cocci: *staphylococcus* |
| 2075 | Negative | / | / | / | |
| 3060 | Yeasts | ++ | ++ | ++ | |
| 2080 | Negative | / | / | / | |

TABLE VD

Cultures under anaerobic and aerobic conditions and $CO_2$:

| Haemo No. | Germs identified at the hospital | Culture condition | Germs identified on blood agar, according to the invention | | |
|---|---|---|---|---|---|
| | | | Without microbeads | 25 μL of microbeads | 50 μL of microbeads |
| 1081 | *E.coli* | Aerobic | +++ | +++ | +++ |
| | | $CO_2$ | ++ | ++ | |
| | | Anaerobic | ++ | ++ | ++ |
| 6032 | *Enterobacter cloaceae* | Aerobic | +++ | +++ | +++ |
| | | Anaerobic | ++ | ++ | ++ |
| 4362 | *Pseudomona aeruginosa* | Aerobic | +++ | +++ | +++ |
| | | Anaerobic | / | / | / |

The invention claimed is:

1. In vitro method for detection and/or quantification and/or identification of bacteria present in a fluid medium M constituting a biological material, a method in which, in a known manner, a suspension of microbeads in a liquid suspension medium is prepared, said microbeads being delimited by an outer surface constituted by a solid polymer material capable of binding proteins, characterized by the fact that it comprises the following stages:
   a) in an appropriate buffer, a loading of the microbeads in the suspension with β2GPI proteins is ensured by coupling with a sufficient quantity of β2GPI proteins, either passively in a suspension medium or using a known chemical binding protocol;
   b) in a container, said microbeads loaded with β2GPI proteins are brought into contact with the fluid medium M under appropriate conditions in order to ensure, without the presence of oxidizing metal ions, sufficient binding of the bacteria to the β2GPI proteins carried by the microbeads;
   c) the microbeads thus prepared are separated from their suspension medium, said suspension medium is removed from the container in order to obtain a residue with a high concentration of bacteria;
   d) and the bacteria are detected and/or quantified and/or identified, starting from the concentrated residue thus obtained.

2. Method according to claim 1, characterized by the fact that the microbeads constituting said residue are washed, brought into contact with a culture medium capable of allowing their multiplication and, in a known manner, the bacteria are quantified and/or identified from said culture medium.

3. Method according to claim 2, characterized by the fact that in order to allow the multiplication of the bacteria of the medium M bound to the microbeads and they are incubated on the culture medium is ensured for an appropriate period and at an appropriate temperature.

4. Method according to claim 1, characterized by the fact that the fluid medium M is a haemoculture.

5. Method according to claim 4, characterized by the fact that after obtaining the residue with a high concentration of bacteria, the microbeads are resuspended in a TSB broth, and this broth is applied to a "Columbia" sheep blood culture medium.

6. Method according to claim 1, characterized by the fact that the bacteria are identified by Gram staining and/or by sub-cultures on selective or non-selective medium.

7. Method according to claim 1, characterized by the fact that the bacteria are quantified by optical density reading, by ATP-metry or by PCR of lysate.

8. Method according to claim 1, characterized by the fact that the solid material constituting the outer surface of the microbeads is chosen from the group formed by the plastics and the elastomers, said material carrying or not carrying reactive groups grafted to the outer surface of the microbeads in order to ensure a chemical bond to the β2GPI proteins.

9. Method according to claim 1, characterized by the fact that microbeads having a substantially spherical shape and an average diameter comprised between 1 and 100,000 nm are chosen.

10. Method according to claim 1, characterized by the fact that microbeads having a core formed by one (or more) particle(s) of magnetic material are chosen in order to allow their separation from the suspension medium using a magnetic field.

11. Method according to claim 1, characterized by the fact that the microbeads are separated from their suspension medium by centrifugation.

12. Method according to claim 1, characterized by the fact that the loading of the microbeads with β2GPI proteins is carried out by placing them in a liquid suspension medium which contains, in aqueous solution, from $10^{-6}$ to 100 mg of β2GPI per gram of dry weight of microbeads, the concentration of β2GPI in the medium being comprised between $10^{-5}$ and 10 μg/μl and by stifling the suspension thus constituted for 15 to 60 minutes at a temperature comprised between 30 and 45° C.

* * * * *

UNITED STATES PATENT AND TRADEMARK OFFICE
CERTIFICATE OF CORRECTION

PATENT NO.        : 8,383,353 B2                                               Page 1 of 1
APPLICATION NO.   : 12/865823
DATED             : February 26, 2013
INVENTOR(S)       : Ilias Stefas It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 372 days.

Signed and Sealed this

First Day of September, 2015

Michelle K. Lee
*Director of the United States Patent and Trademark Office*

SEQUENCE LISTING

<160> NUMBER OF SEQ ID NOS: 2

<210> SEQ ID NO 1
<211> LENGTH: 29
<212> TYPE: DNA
<213> ORGANISM: Artificial Sequence
<220> FEATURE:
<223> OTHER INFORMATION: synthetic

<400> SEQUENCE: 1
gtgctgcaga gagtttgatc ctggctcag                            29

<210> SEQ ID NO 2
<211> LENGTH: 31
<212> TYPE: DNA
<213> ORGANISM: Artificial Sequence
<220> FEATURE:
<223> OTHER INFORMATION: synthetic

<400> SEQUENCE: 2
cacggatcct acgggtacct tgttacgact t                         31